US010779992B2

(12) United States Patent
Delfino et al.

(10) Patent No.: US 10,779,992 B2
(45) Date of Patent: Sep. 22, 2020

(54) HEARING PROTECTION DEVICES AND ATTENUATION BUTTON FOR SAME

(71) Applicant: Fader Plugs, LLC, Bethlehem, PA (US)

(72) Inventors: Blaise Delfino, Bethlehem, PA (US); Gregory Delfino, Bethlehem, PA (US); Kevin Skeuse, Stockton, NJ (US); Paul Dowd, Scarsdale, NY (US)

(73) Assignee: Fader Plugs, LLC, Bethlehem, PA (US)

( * ) Notice: Subject to any disclaimer, the term of this patent is extended or adjusted under 35 U.S.C. 154(b) by 344 days.

(21) Appl. No.: 15/719,862

(22) Filed: Sep. 29, 2017

(65) Prior Publication Data

US 2018/0098885 A1 Apr. 12, 2018

Related U.S. Application Data

(60) Provisional application No. 62/407,215, filed on Oct. 12, 2016.

(51) Int. Cl.
*A61F 11/08* (2006.01)

(52) U.S. Cl.
CPC ......... *A61F 11/08* (2013.01); *A61F 2011/085* (2013.01)

(58) Field of Classification Search
CPC .... A61F 11/08; A61F 2011/085; A61F 11/00; A61F 11/06; A61F 2011/659; A61F 2011/145; G10K 11/175; H04R 1/1016; H04R 1/1083; H04R 25/659; H04R 2460/11

USPC .......... 181/129–135; 128/864–868; 381/328–329, 380, 325
See application file for complete search history.

(56) References Cited

U.S. PATENT DOCUMENTS

| | | | |
|---|---|---|---|
| 3,800,791 A | 4/1974 | Visor | |
| 4,540,063 A | 9/1985 | Ochi et al. | |
| (Continued) | | | |

FOREIGN PATENT DOCUMENTS

WO 2014107319 7/2014

OTHER PUBLICATIONS

3MTM Military Combat Safety Gear, Combat ArmsTM Earplugs http://multimedia.3m.com/mws/media/851487O/combat-arms-earplugs.pdf.

(Continued)

*Primary Examiner* — Anna K Kinsaul
*Assistant Examiner* — Trisha Talapatra
(74) *Attorney, Agent, or Firm* — Wendy W. Koba

(57) ABSTRACT

A manually, selectively attenuating earplug button is disclosed, for insertion into a cavity of an earplug of a hearing protection device The earplug button comprises a nested configuration of a first housing member (including a first opening to receive sound from an ambient environment) and a second housing member, surrounding the first housing member and including a second opening to output at least a portion of the sound passing through an audio channel located between said first and second openings The first and second housing members include sidewall apertures for permitting a wearer to manually adjust the amount of sound admitted to the wear's ear from said ambient environment by rotating the first housing member (and thus its sidewall aperture) with respect to the second housing member.

4 Claims, 4 Drawing Sheets

(56) References Cited

U.S. PATENT DOCUMENTS

| | | | |
|---|---|---|---|
| 5,002,151 A * | 3/1991 | Oliveira | A61F 11/08 181/130 |
| 5,113,967 A | 5/1992 | Killion et al. | |
| 6,082,485 A | 7/2000 | Smith | |
| 6,148,821 A | 11/2000 | Falco | |
| 7,182,087 B1 | 2/2007 | Marsh | |
| 7,512,243 B2 | 3/2009 | Haussmann | |
| 8,113,207 B2 | 2/2012 | Gehling et al. | |
| 8,345,906 B1 | 1/2013 | Kataw | |
| 8,514,870 B2 | 8/2013 | Ma et al. | |
| 8,820,470 B2 | 9/2014 | Brown | |
| 8,931,489 B2 | 1/2015 | Smith | |
| 9,131,308 B2 | 9/2015 | Kraft et al. | |
| 2006/0045299 A1 | 3/2006 | Haussmann | |
| 2008/0276945 A1 | 11/2008 | Rosen | |
| 2012/0318605 A1 * | 12/2012 | Brown | A61F 11/12 181/126 |
| 2013/0011509 A1 * | 1/2013 | Schumaier | A61F 11/08 425/318 |
| 2014/0190494 A1 * | 7/2014 | Ely | A61F 11/12 128/868 |
| 2014/0270257 A1 * | 9/2014 | Bauman | G10K 11/178 381/109 |
| 2015/0036834 A1 | 2/2015 | Bauman et al. | |
| 2015/0136148 A1 * | 5/2015 | Cheng | A61F 11/08 128/868 |
| 2017/0156932 A1 * | 6/2017 | Chae | A61F 2/0095 |

OTHER PUBLICATIONS

Westone TRU Universal WM25 Full Frequency Earplugs—Universal Fit http://www.sweetwater.com/store/detail/TruWM25?adpos=1o2&creative=55678058761&device=c&matchtype=&network=s&gclid=CIOz4a-jnM8CFcEehgodnx4IVA.

Alpine Hearing Protection https://www.alpinehearingprotection.com/earplugs/musicsafe-pro/.

The High Notes of Musicians Earplugs http://www.hearingreview.com/2014/07/high-notes-musicians-earplugs/.

Silicone Keypad Design Guide, 01 Silicone Material http://www.abatek.com/designguide/01SiliconeMaterial.html.

ER•20® XS High-Fidelity Earplugs http://www.etymotic.com/consumer/hearing-protection/er20xs.html.

Google Search results for Adjustable Attenuation Earplus https://www.google.com/search?tbm=pts&q=adjustable+attenuation+earplugs&cad=h.

Vincent, James "These fancy earbuds have a built-in slider for letting in more or less noise" https://www.theverge.com/circuitbreaker/2017/4/24/15405222/adjustable-earbuds-dbud-kickstarter Apr. 24, 2017.

Knops—The volume button for your ears https://www.kickstarter.com/projects/knops/knops-the-volume-button-for-your-ears.

3470 Fader Plug Concept Review Jul. 11, 2016.

* cited by examiner

HEARING PROTECTION DEVICES AND ATTENUATION BUTTON FOR SAME

CROSS-REFERENCE TO RELATED APPLICATIONS

This application claims priority under 35 U.S.C. § 119(e)(1) from U.S. Provisional Application Ser. No. 62/407,215, filed Oct. 12, 2016, the contents of which are incorporated herein by reference.

FIELD OF THE INVENTION

This invention relates generally to earplugs and more specifically to attenuating earplug button constructions useful in hearing protection.

BACKGROUND

It is well documented that repeated or prolonged exposure to sounds of sufficiently high sound pressure will cause temporary or permanent hearing loss, including in some instances, deafness. Injurious noises such as those caused by gun fire or jet engines, and the like, are often composed of a mixture of sound wave frequencies of varying intensities. These frequencies are in both the high and low frequency bands and have an intensity sufficient to cause hearing problems. Individuals who are frequently exposed to such sounds, such as military personnel and airline baggage handlers, run the risk of incurring serious injuries to their hearing. Hearing protection in such environments is needed to prevent a loss in hearing acuity and the gradual increase in the threshold of hearing resulting from extended exposures to loud noises.

Sound attenuation devices are known which specifically address this problem. These devices include conventional foam earplugs, earmuffs, and the like. While these devices protect against the effects of overexposure to sound having dangerous frequencies and intensities, they sometimes create a new danger in that they shut out all environmental sounds, including those of speech and warning.

In an effort to overcome this problem of nearly 100% attenuation, some hearing protection earplugs have been provided with a selective attenuation capability, wherein the earplug can offer the wearer the ability to choose between two different performance settings for the earplug depending upon the environment of the wearer. In the first mode, for example, sound attenuation is low for a specific range of intensities above those in the specified range.

Selective attenuation is especially effective for the loudest noises. A sample application of an earplug in the selective attenuation mode is the intelligible speech transmission in a noisy environment caused by pulsed noises, such as gunshots, for example. In the maximum attenuation mode, these earplugs stop all sounds throughout the intensity range, regardless of their intensity.

And still others have been disclosed as having adjustable attenuation, such as, for example: U.S. Pat. Nos. 8,113,207; 3,800,791; 6,082,485; 7,512,243; 8,514,870; 8,345,906; 8,931,489; 6,148,821; 4,540,063; 5,113,967; 9,131,308 and 8,820,470; and U.S. Pat. Appl. Nos. 2014/0190494 and 2008/0276945; and WIPO Pat. Appl. No. WO2014107319A1; which are all incorporated herein by reference.

Perhaps no one appreciates the sense of hearing as much as musicians. Almost all musical instruments are capable of producing damaging sound levels, and musicians are at increased risk of developing music-induced hearing disorders. Moderate-attenuation, high fidelity hearing protectors, on the other hand, reduce the risk of music-induced hearing disorders while allowing the musician to hear clearly.

Applied to earplugs, the term "high-fidelity" means that earplugs reduce sound levels while maintaining, as closely as possible, the quality of the original sound. The average open ear canal has an acoustic resonant peak of approximately 17 dB at 2700 Hz. Placing an earplug in the ear removes this natural resonance, resulting in unbalanced attenuation that makes music and voices sound muffled and unclear. A high-fidelity earplug is designed to match the open ear response by adding back the resonant peak. Attenuation should be as even as possible across the frequency spectrum to preserve the timbre and quality of sound, so that sound heard while wearing high-fidelity earplugs is essentially the same as the original, only quieter Custom musician's earplugs consist of a diaphragm (attenuator "filter" or "button"), which functions as an acoustic compliance, and a custom earmold or earplug, in which the volume of the air in the sound bore acts as an acoustic mass. The combination of the two produces a resonance at approximately 2700 Hz, resulting in smooth, flat attenuation across the frequency range. Attenuator buttons are interchangeable, which allows musicians to choose the filter strength most appropriate for a given situation. Buttons for various instruments and situations, for example, drums versus solo vocals, can be selected, for example, a choice of 9, 15, or 25 dB filters. Since many musicians perform in a variety of groups and venues, they may need two, or even all three, sets of interchangeable buttons.

Electronic musician's earplugs are also available which can automatically adapt to changes in sound levels, providing protection when needed and natural hearing when sound levels are low. For example, a musician playing in a symphony may need protection from sustained high-level sound and loud transients (e.g., cymbal), but also need to hear the conductor's instructions across the stage during rehearsal.

While these publically available and patented earplugs have been sometimes commercially successful, they typically are not customizable like the fixed attenuation of the ETY-Plugs® product, offer limited choices in the number of frequencies or intensities they can manage, like the limited replaceable buttons of the Musicians Earplugs™ product which require removal to insert a different filter, or tend to be very expensive and/or complex to manufacture like the MusicPRO (active) Musicians Earplugs product.

SUMMARY OF THE INVENTION

The present invention provides in a first embodiment, a manually, selectively attenuating earplug button, for insertion into a cavity of an earplug or earmold of a hearing protection device, comprising: a longitudinal central axis; a first opening to receive sound from an ambient environment; a second opening to output at least a portion of said sound to an ear of a listener (preferably through a sound bore of an earplug); an audio channel located between said first and second openings, said audio channel having a sound attenuation valve for permitting a wearer to manually adjust the amount of sound admitted to the wear's ear from said ambient environment.

In a second embodiment of this invention a manually, selectively attenuated earplug button for insertion into an earplug of a hearing protection device, is provided. The button includes a longitudinal central axis, a first opening to receive sound from an ambient environment, such as concert music and the like, a second opening to output at least a portion of the sound to an ear of a listener and an audio channel located between the first and second openings. The audio channel has an inner chamber and an outer chamber disposed generally along the longitudinal central axis. The button also includes first and second housing members coaxially connected together and disposed along said central axis so that said first housing member can coaxially rotate at least partially within said second housing member, while said second housing member is inserted in a relatively fixed position within an earplug. The first housing member includes the inner chamber of the audio channel and the second housing member includes the outer chamber of the audio channel. The first housing member includes a first sidewall aperture which is in audio communication with the inner chamber and the first opening. The second housing member has a second sidewall aperture which is in audio communication with the outer chamber and the second opening. The button further includes a sound attenuation turning knob which is provided at an outer end of the first housing member. The turning knob can be manually rotatable to rotate the first housing member axially relative to said second housing member between a first highly attenuated sound position in which said first and second sidewall apertures are not in alignment and at least a plurality of further audio communication positions in which the first and second sidewall apertures are at least partially aligned to different degrees to provide sound at a plurality of different sound attenuation levels to the ear of the listener.

In a further embodiment of the present invention, the button could further include selectively interlocking tooth means for providing a plurality of fixed settings for subsequent manual adjustment when the turning knob is manually rotated to rotate the first housing member coaxially at least partially within the second housing member.

In still a further embodiment of the present invention, an earplug of a hearing protection device is provided comprising a soft resilient material having a hardness on the Shore A Durometer hardness scale. The earplug has a molded cavity therein for receiving an earplug button having sound attenuation control capability.

The present invention provides for easy removal and replacement of earplug buttons on-the-fly, so that expensive or custom made earplugs or earmolds can be washed and reused over and over again, or alternatively, disposable foam earplugs could be discarded while reusing the earplug button. The ear plugs are desirably molded to have an internal cavity sized to fit a significant portion of the earplug buttons of the present invention. One or more filters could also be added to the earplug buttons of this invention to add an additional layer of attenuation or hearing refinement.

The embodiments of the present invention provide for low cost and disposable earplug buttons having selective sound attenuation control, as well as earplugs having molded cavities for receiving such buttons. The preferred buttons can provide fine-tuned adjustments to hearing protection devices and earplugs by enabling relatively full attenuation, where sound is substantially prevented from entering the ear canal, to multiple attenuation settings so that the wearer can adjust the earplugs or hearing protection device to his or her own comfort level. The preferred constructions are low cost, offer 3-20 or more settings and can be fitted into both conventional foam, rubber and silicone earplugs, or into custom made molded silicone or soft PVC earplugs. They have a small form factor which can be manufactured into one size-fits all flexibility, regardless of the size of the wearer's ear. They are also simply designed from a mechanical perspective, easy to manufacture and easy to change.

Whereas prior art adjustably attenuated earplugs were equipped with an entire ear plug, provided limited settings or merely provided replaceable filters for selective attenuation, the present earplug buttons can be replaced at any time, and thereafter manually adjusted during use by the wearer to many different settings, or swapped out manually to another earplug button, having different or the same attenuation settings, whenever more or less attenuation is needed. These earplug buttons are ideal for musicians who would like to communicate with one another in-between sets, for example, but still provide the flexibility of different attenuation levels on-the-fly.

BRIEF DESCRIPTION OF THE DRAWINGS

The accompanying drawings illustrate preferred embodiments of the invention as well as other information pertinent to the disclosure, in which.

DETAILED DESCRIPTION

The present disclosure provides a selectively attenuating earplug button that can be used with prefabricated foam, rubber, silicone or custom made molded soft resilient earplugs. The preferred earplug button may be adjusted between multiple operating modes to alter the performance of the earplug. The selective attenuating earplug button provides, in a first embodiment, at least a first setting that allows sound having a specified frequency or intensity to pass to the ear canal of a wearer with little or no attenuation, and a second setting providing a maximum level of attenuation across a certain frequency and/or intensity range, and one or more intermediate (or even an infinite number of) settings that permit varying degrees of attenuation of sounds in a different frequencies or intensity ranges. The selective capability of the earplug button of this embodiment allows a wearer to dial-in the degree of desired sound attenuation depending on the current environment surrounding the wearer. A selective attenuation setting may be selected when a wearer desires to hear speech or warning signals in a noisy environment, for example, while still being protected from dangerous noises. Such a setting may be particularly desirable when the noisy environment includes loud concert music, aircraft or motor racing noises, and the like. A maximum attenuation setting may be selected to minimize most sounds throughout the frequency range from entering an ear canal, regardless of intensity.

Figure 7:
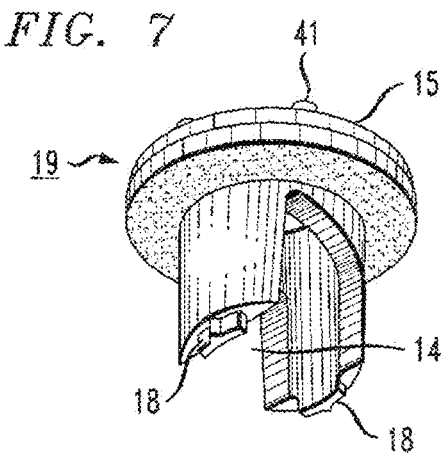
FIG. 7: is a bottom perspective view of an alternative embodiment of the first housing member, including a tooth member.
Figure 8:
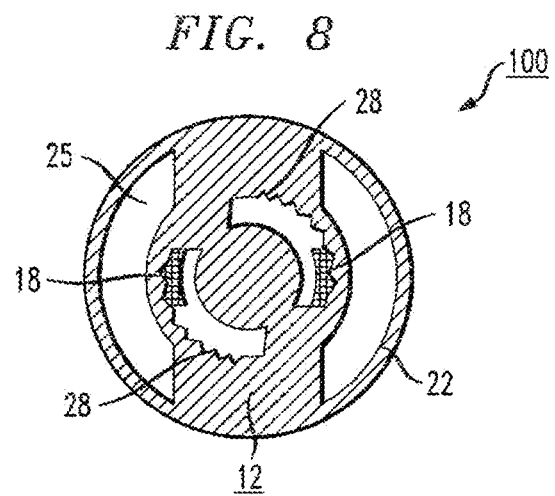
FIG. 8: is a bottom view of the alternative embodiment of the earplug button, showing the tooth member of the first housing member in an interlocking arrangement with a set of teeth formed in the second housing member.
Figure 9:
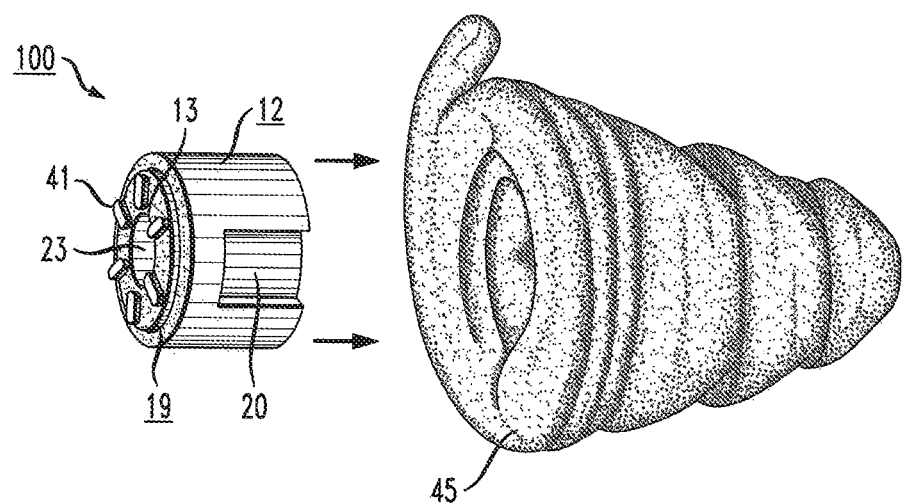
FIG. 9: is a left side perspective and exploded view of the earplug button of FIG. 1, in combination with a hollowed-out soft resilient earplug.
Figure 10:
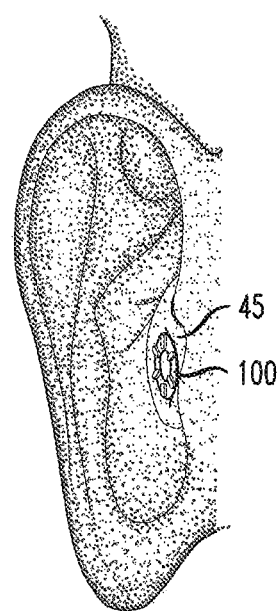
FIG. 10: is a left side perspective view of a human ear (in phantom), illustrating the positioning of the button and earplug combination of FIG. 9.

With reference to the figures and in particular, to FIGS. 1-8 thereof, there is shown a preferred manually, selectively attenuating earplug button 100, for insertion into an earplug or earmold, for example earplug 45 in FIGS. 9 and 10. The earplug button 100 includes a longitudinal central axis 11, shown in FIG. 1. As more clearly shown in FIGS. 2 and 4, the button 100 includes a first opening 13 to receive sound from an ambient environment and a second opening 22 to output at least a portion of the sound to an ear of a listener. These sounds could be loud music, machinery noise, or the sound of a jet or race car engine, for example. The preferred earplug buttons 100 are ideal for musicians, since they allow multiple settings, such as 3 to 20 settings (such as for example, 9, 15, or 25 dB of attenuation), for various attenuation levels of sounds of high to medium sound pressure. In the event a performer is standing on stage between a drummer and a back-up singer, she can adjust the earplug nearest the drummer to a higher setting and the earplug nearest the backup singer to a relatively lower setting to balance the sound 55 she is receiving to a safe level without using two different earplugs or filters.

The earplug button 100 further includes an audio channel located between the first opening 13 and the second opening or openings 22. The audio channel includes an inner chamber, shown for example as inner chamber 23 and an outer chamber, or chambers 25, disposed generally along the longitudinal central axis 11.

Figure 1:
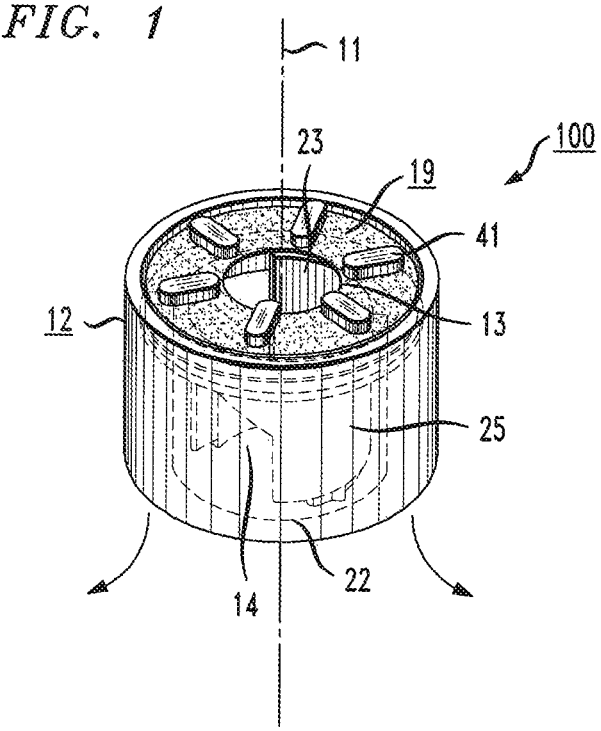
FIG. 1: is an isometric view of an earplug button of this invention.
Figure 2:
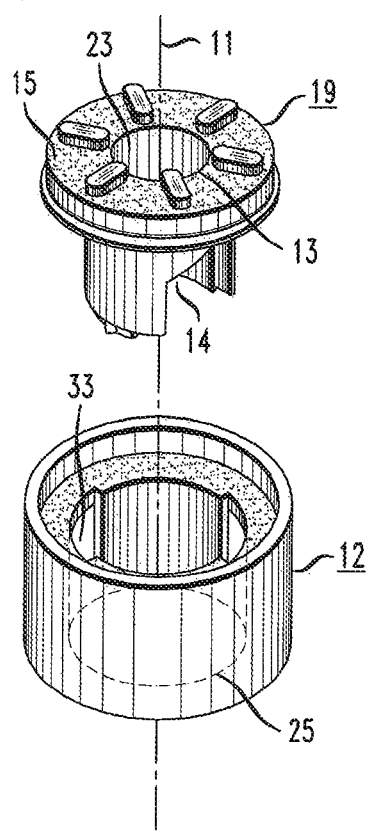
FIG. 2: is an exploded view of the earplug button of FIG. 1.

The earplug button 100 further includes a first housing member 19 and a second housing member 12 which are preferably coaxially connected together, as shown in FIGS. 1 and 2, and disposed along the longitudinal central axis 11, so that the first housing member 19 can coaxially rotate at least partially within the second housing member 12, while the second housing member 12 is inserted in a relatively fixed position within an earplug 45, as substantially shown in FIG. 10.

Figure 3:
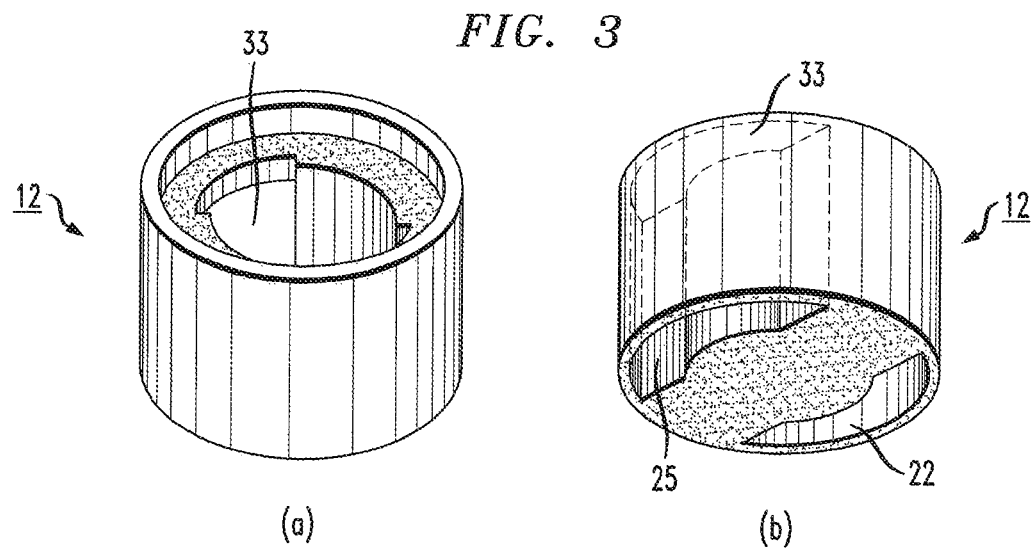
FIG. 3: contains top and bottom isometric views of the second housing member of the earplug button, with FIG. 3(*a*) being a top isometric view and FIG. 3(*b*) being a bottom isometric view.
Figure 4:
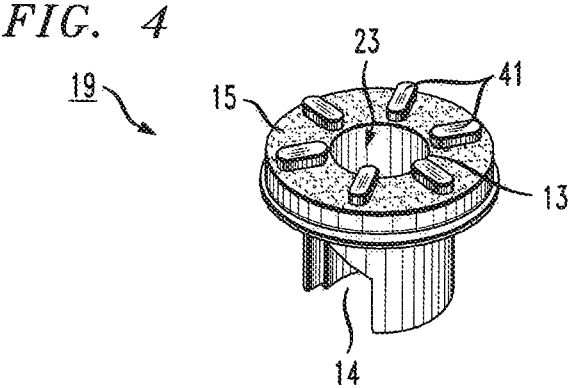
FIG. 4: is an isometric view of the first housing member of the earplug button.

The first housing member 19, as shown in FIGS. 2 and 4, includes the inner chamber 23 of the audio channel. The second housing member 12, as shown in FIGS. 2 and 3, includes the outer chamber, or chambers 25 of the audio channel. The first housing member 19 includes a first sidewall aperture(s) 14 shown in FIGS. 2, 4 and 7, which is in audio communication with the inner chamber 23 and the first opening 13. The second housing member 12 shown generally in FIGS. 2 and 3, includes a second sidewall aperture, or apertures 33, which is in audio communication with the outer chamber, or chambers 25 and the second opening, or openings 22.

Finally, the preferred earplug button 100 includes a sound attenuation turning knob 15 shown in FIGS. 1, 2, 4-7 and 9, which is provided at an outer end of the first housing member 19. The turning knob 15 is manually rotatable to rotate the first housing member 19 axially relative to the second housing member 12 between a first highly attenuated sound position in which the first and second sidewall apertures 14 and 33 respectively, are not in alignment and at least a plurality of further audio communication positions in which the first and second sidewall apertures 14 and 33 are at least partially aligned to different degrees to provide sound at a plurality of different sound attenuation levels to the ear of the listener.

Figure 5:
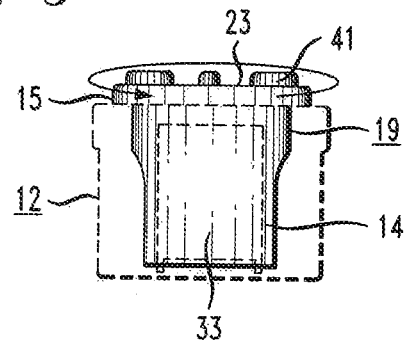
FIG. 5: is a side view of the earplug button, illustrating a fully attenuated, or closed setting of the earplug button.
Figure 6:
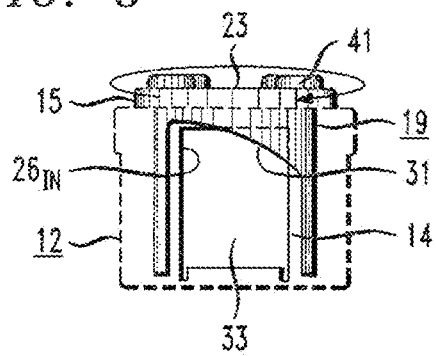
FIG. 6: is a side view of the earplug button, illustrating a fully open setting.

Also in FIG. 5, there is shown an operation of the earplug button 100, whereby the first sidewall aperture 14 (shown as a pair in FIG. 7) is not in communication with the outer chamber 25 and second opening 22 of the second housing member 12. In this position, the earplug button 100 provides nearly full attenuation, with sound being blocked as it comes into first opening 13 and inner chamber 23 by the inner wall surface of the second housing member 12. As the turning knob 15 is rotated to provide axial motion to the first housing member 19 it causes a rotation within the second housing member 12, the first sidewall apertures 14 begin to align with the pair of second sidewall apertures 33, shown in FIG. 6. At first the overlap is small and only a little of the ambient sound is passed through to the outer chambers 25 and second openings 22, and consequently to the ear of the wearer. But as the turning knob 15 continues to rotate, more and more of the first sidewall apertures 14 are exposed or overlap with the second sidewall apertures 33 until substantially all of the first sidewall aperture 14 is enveloped, by the second sidewall aperture 33 (or made coextensive with it), providing very little attenuation, for allowing wearers to hear soft conversations in a relatively quiet environment, for example.

In order to provide relative axial rotation between the first housing member 19 and the second housing member 12, it is desirable to prevent the rotation of the second housing member 12 after it is inserted into the earplug 45. This can be accomplished by sidewall indents 20, shown in FIG. 9. The indents 20 can be molded into the second housing member 12 during injection molding. The inner wall of the sidewall indents desirably also provides a matching surface to the outside wall of the first housing member 19 so that the first housing member 19 can rotate smoothly along the inner wall of the sidewall indents 20 of the second housing member 12. Thus, the sidewall indents 20 provide dual functions in this preferred embodiment. Additionally, it can be seen in FIG. 6 that the first sidewall apertures 14 may have a reduced cross-section traversing the upper end of the first sidewall aperture 14 shown in FIG. 6. Another sidewall aperture 14 is preferably disposed on the opposite side of the first housing member 19, as shown in FIG. 7. The width of the openings formed by apertures 14 is shown as being smaller in FIG. 2 because of the sloped or tapered edge 31 shown in FIG. 6. The tapering of the first sidewall aperture 14, or apertures, allows for a logarithmic or non-linear attenuation of the sound entering the ear canal. It also allows slightly greater attenuation between settings than if the top edge of the first sidewall aperture 14 was horizontal or flat.

In a further embodiment of the present invention as shown FIGS. 7 and 8, the earplug button 100 may further include selectively interlocking tooth means, for example, including first housing teeth or tooth 18 and second housing teeth 28 for providing a manual adjustment between a plurality of attenuation settings when said turning knob 15 is manually rotated to rotate the first housing member 19 coaxially at least partially within the second housing member 12. These teeth are generally located near the second opening 22 of the earplug button 100 in the embodiment shown in FIG. 8. As shown in FIG. 8, there are several female grooves in the second housing teeth 28 and one male tooth in the first housing teeth or tooth 18, so there are several different settings shown in the earplug button 100. It is expected that 3-20, and possibly more settings, can be provided by increasing the number of teeth, while providing accurate and predictable settings. Of course this means that the wearer must adjust the setting to full attenuation in the event of a threat from ear-damaging noise, but this is simply done by rotating the turning knob 15 by using one's fingers to locate the knob indicators 41 shown in FIG. 1, which are raised from the surface of the turning knob 15, and rotating the turning knob 15 either clockwise or counter-clockwise, depending upon which setting the device is in.

In a further preferred embodiment of the present invention, the first housing teeth or tooth 18 and second housing teeth 28 of FIG. 3 are made of resilient materials, such as plastic, so that upon an axial rotation of the first housing member 19 within the second housing member 12, the first housing teeth 18 can pass over consecutive teeth in the second housing teeth 28 and provide an audible click as the earplug button 100 goes from one attenuation setting to another. This clicking sound along with the readily accessible turning knob 15 and knob indicators 41 will provide a high degree of accuracy for wearers of the earplug button 100. In more preferred embodiments of the present invention, the second housing teeth 28 can be made in slightly graduated sizes, so that the movement of the first housing teeth or tooth 18 over the second housing teeth 28 will produce a louder (for larger teeth) or softer (for smaller teeth) sound 55 as the attenuation setting is increased or decreased.

The earplug button 100 of the present invention preferably includes only two components, the first housing member 19 and second housing member 12, although three or more could also be used They are preferably injection molded thermal plastic components, but they could easily be made out of metal or ceramic components and made with conventional manufacturing processes. The earplug buttons 100 are designed in a preferred embodiment, to be inserted into an earplug 45 which can be of a conventional design, quite often molded to the shape of the ear of the wearer. Such molding techniques are known in the relevant art and any suitable conventional molding techniques may be used to produce the earplug button 100 of the present invention. The earplug button 100 may be manufactured by using the procedures and details disclosed in U.S. Pat. No. 4,867,149 (hereby incorporated herein by reference), and preferably the earplug button 100 is composed of the same polymeric material, such as nylon, polystyrene, polypropylene, polyethylene, or suitable low cost thermoplastic material.

In some embodiments, the attenuating earplug buttons 100 may be incorporated into hearing protection kits, such as those including resilient foam or silicone or rubber earplugs. In such applications, the earplug button 100 is inserted into resilient earplugs 45 as shown in FIGS. 11 and 12. The earplug 45 or ear mold has been hollowed out, e.g. via molding or machining, etc., to provide a channel or sound bore along its length and a recess for the button 100. Molding allows for custom made earplugs 45 that can be molded to match the inner and/or outer ear canal of the user. This design also permits the earplug button 100 to be replaced, when defective, or when different attenuation properties are needed a different tuned earplug button 100 can be inserted, without discarding the custom molded earplugs.

As shown in FIGS. 9 and 10, this invention also provides an earplug 45 of a hearing protection device, comprising a soft resilient material having a hardness on the Shore A or Shore 00 Durometer hardness scales. There are many known resilient polymeric materials which may be utilized effectively in the fabrication of the preferred earplugs 45 of the present invention. In one preferred embodiment, the resilient earplugs 45 can comprise a soft resilient polymeric foam adapted in size and shape to be inserted into the human ear canal and acoustically sealed along its perimeter. In other embodiments the resilient earplug 45 is composed of a polyurethane foam, natural rubber, neoprene rubber, SBR rubber, silicone rubber, EPDM rubber, polybutadiene rubber, polyurethane, elastomers, ethylene vinyl acetate elastomers, elastomers, based on acrylic acid precursors and vinyl halide polymers, or combinations thereof. All are generally suitable materials for construction which can generally be procured from commercial sources. Thermoplastic compositions such as the family of thermoplastic injection moldable elastomers can be used. These thermoplastic compositions are available in a considerable range of Shore A and Shore 00 Durometer hardness values. These compounds can be thermally formed into intricate shapes by any conventional thermoplastic molding technique, or poured into a mold made from a cast of a patient's ear. Earplugs produced can generally be sterilized or cleansed without degradation thereof.

Applicant has found that the earplug buttons 100 work better if installed in a more rigid, but still comfortable, earplug, e.g., having a Shore A hardness, such as a molded, custom-made silicone earplug, or a tiered silicone cone shaped earplug. Alternatively, if the earplug buttons 100 are installed in normal colored-foam compressible foam earplugs, the wearer won't be able to compress the earplugs fully to insert them deeply into their ears, so he or she may have to try inserting the earplugs into his or her ears multiple times to get the right fit, and feel when they're seated properly.

The preferred earplug 45 has a molded cavity therein sized for receiving an earplug button 100 having sound attenuation control capability. The cavity or recess can vary from about 0.125" to about 1' in diameter and or depth, and can be molded around the earplug insert 100. Preferred buttons 100 can be glued, molded into, or unglued and inserted into the cavity of the earplug 45. If merely inserted, they are completely transferable to different foam or silicone plugs if desired. To minimize fall out, the buttons 100 can be made to frictionally fit within the earplug 45. To insert the button 100, the wearer can stretch the back of the earplug 45 and re-insert it.

If the earplug 45 is molded over the button 100, the hard plastic of the button 100 can be made to have a melt or adhesive bond with the earplug 45, or no bond at all. Over-molding manufacturing processes can be used so that the interface between these components can include one or more interlocking inner and outer wall extended and impressed surfaces which, for example, can be formed by the impressions of sidewall indents 20, or a recessed rim around the earplug button 100 and matching extensions or a ring on the inside wall of the earplug 45 (not shown). Other shapes other that those shown could be used, and the earplug cavity could have impressions itself molded to receive extended surfaces of the earplug button 100, instead. The idea of selectively mechanically locking the earplug 45 and earplug button 100 together can be accomplished in many different ways, including using friction alone, threads, and/or a mechanical lock and/or adhesive, so long as the resulting effect is to restrain the earplug button 100 so that it can be manually adjusted by the wearer without substantially moving it within the earplug 45.

In some embodiments, the attenuating earplug buttons 100 may include multiple attenuator buttons 100 each having the same maximum attenuation which may be used as replacements or backups. In other embodiments, the plurality of buttons 100 may include an assortment of different attenuator valves (such as, the valve of the preferred button 100, a conical pin valve with a conical mating seat; a compressible sound attenuation media which attenuates more sound as it is compressed and becomes denser, and/or button filters). The valves and optional filters can have different maximum attenuations such as 9, 15, or 25 dB of attenuation, or multiple settings, such as 9, 15, or 25 dB settings within a single button 100 (which can made to further vary over portions of typical hearing frequencies), or set attenuation increments of 2 dB, per click or set rotation of the turning knob 15, so that a wearer can select the amount of protection needed based on expected exposure to noises or loud environmental sounds, on-the-fly, without having to take out the earplugs 45.

It is often desirable to provide a pair of earplugs tethered together by means of a length of cord, rope or tether. A combination of two sets of earplug buttons 100 and earplugs 45 can be joined together similarly. Such a tethered earplug construction can serve to prevent accidental dropping or loss. This can be useful, for instance, where the earplugs 45 are to be utilized in an industrial food processing environment or in an environment where a dropped earplug 45 or button 100 would likely be contaminated so as to be rendered unusable or lost altogether.

The buttons 100 are compatible with the left and right ears, and turn in "opposite" directions (clockwise and counterclockwise) for opening and closing the audio channel. Alternatively, the buttons 100 can be made so that they both operate in a clockwise or counterclockwise direction, designating one button for the right ear and one button for the left ear.

From the foregoing, it can be realized that this invention provides improved earplug buttons 100 which provide the wearer with interchangeability between, disposable foam, molded or hollowed out conventional or custom earplugs for hearing protection devices. The earplug buttons can have a more inexpensive construction than former devices, and a greater number of attenuation settings. Although various embodiments have been illustrated, this is for the purpose of describing but not limiting the invention. Various modifications which will become apparent to one skilled in the art, are within the scope of this invention described in the attached claims.

LIST OF FIGURE REFERENCE NUMERALS

100—earplug button
11—longitudinal central axis
12—second housing member
13—first opening to receive sound
14—first sidewall aperture(s)
15—turning knob
18—first housing teeth or tooth
19—first housing member
20—sidewall indents (rotation restraining means)
22—second opening to output sound
23—inner chamber
25—outer chamber(s)
28—second housing teeth
31—tapered edge (top or bottom)
33—second sidewall aperture(s)
41—knob indicators
45—earplug
50—ear
55—sound

What is claimed is:

1. A manually-adjustable earplug button for insertion into an earplug of a hearing protection device, the manually-adjustable earplug button comprising
   a first housing member including a first opening formed along a longitudinal central axis and at least one aperture formed within a sidewall thereof, the first opening defining an input audio port, providing an inner chamber of an audio channel in combination with the at least one aperture; and
   a second housing member disposed to surround the first housing member so as to form a nested configuration while providing a sufficient gap to allow for the first housing member to freely rotate with respect to the second housing member, the second housing member includes a bottom surface for supporting the first housing member and at least one aperture formed within a sidewall thereof, wherein an overlap between the first housing member aperture and the second housing member aperture providing an outer chamber of the audio channel terminating at a second opening, the audio channel being manually adjustable by rotation of the first housing member, controlling the audio channel to adjust the sound attenuation presented at the second opening,
   wherein the first housing member comprises an engaging tooth formed at a lower termination of the sidewall of the first housing member, and the second housing member comprises a plurality of teeth of increasing size disposed around at least a portion of the bottom surface of the second housing member, the plurality of teeth positioned to engage with the tooth of the first housing member upon placement of the first housing member within the second housing member, the rotation of the first housing member with respect to the second housing member creating an audible click, the audible click becoming louder when passing over teeth of increasing size and becoming softer when passing over teeth of decreasing size.

2. The earplug button as defined in claim 1 wherein the earplug button further comprises
   a turning knob disposed on an outer surface of the first housing member, said turning knob having a textured surface to promote manual rotation of the first housing member with respect to the second housing member.

3. The earplug button as defined in claim 1 wherein the second housing member includes a plurality of sidewall indents formed on an outer surface thereof, the plurality of sidewall indents gripping members engaging with a surrounding earplug to maintain stationary position of the second housing member during manual rotation of the first housing member.

4. The earplug button as defined in claim 1 wherein the first housing member and the second housing member are formed of materials selected from the group consisting of: nylon, polystyrene, polypropylene, polyethylene, and thermoplastic.

* * * * *